United States Patent [19]

Mago nee Karacsony et al.

[11] 4,064,249
[45] Dec. 20, 1977

[54] COMPOUNDS WITH ERGOLINE SKELETON

[75] Inventors: Erzsebet Mago nee Karacsony; Jozsef Borsi; Endre Csanyi; Katalin Pik; Lajos Wolf, all of Budapest, Hungary

[73] Assignee: Richter Gedeon Vegyeszeti Gyar Rt., Budapest, Hungary

[21] Appl. No.: 749,398

[22] Filed: Dec. 10, 1976

Related U.S. Application Data

[62] Division of Ser. No. 579,979, May 22, 1975, Pat. No. 4,005,089.

[30] Foreign Application Priority Data

May 28, 1974 Hungary ............................ GO 1272

[51] Int. Cl.$^2$ .................. C07D 457/06; A61K 31/48
[52] U.S. Cl. .................................. 424/261; 260/285.5
[58] Field of Search ...................... 260/285.5; 424/261

[56] References Cited

U.S. PATENT DOCUMENTS

| 2,673,850 | 3/1954 | Stoll et al. ........................ 260/285.5 |
| 3,822,266 | 7/1974 | Karacsony et al. ................ 260/285.5 |
| 3,901,893 | 8/1975 | Karacsony et al. ................ 260/285.5 |
| 4,005,089 | 1/1977 | Karacsony et al. ................ 260/285.5 |

FOREIGN PATENT DOCUMENTS 1,345,546  1/1974  United Kingdom ............... 260/285.5

Primary Examiner—Donald G. Daus
Assistant Examiner—Mary Vaughn
Attorney, Agent, or Firm—Young & Thompson

[57] ABSTRACT

New compounds of the formula

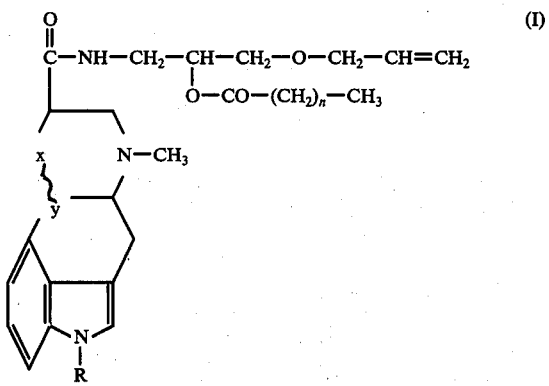

wherein
R is hydrogen or methyl group,
x~~y is a group of the formula

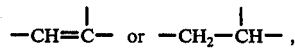

and
$n$ is an integer of from 4 to 10, are prepared by acylating the appropriate lysergic acid-(3'-allyloxy-2'-oxy-propyl)-amide compounds with carboxylic acids of 6 to 12 carbon atoms or with their reactive derivatives. If desired, the new compounds can be converted into their pharmaceutically acceptable acid addition salts.

The above compounds possess prolonged antidepressive activities.

5 Claims, No Drawings

COMPOUNDS WITH ERGOLINE SKELETON

This application is a division of Ser. No. 579,979 filed May 22, 1975 now U.S. Pat. No. 4,005,089.

This invention relates to new compounds with ergoline skeleton and pharmaceutical compositions containing the same.

The new compounds according to the invention correspond to the formula

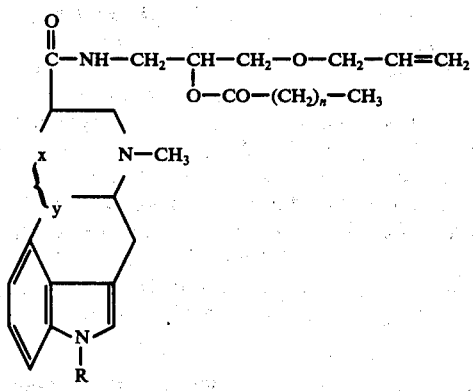
(I)

wherein
R is hydrogen or methyl group,
$\widehat{x\ y}$ is a group of the formula

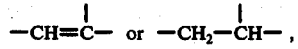

and
n is an integer of from 4 to 10.

The pharmaceutically acceptable acid addition salts of the above compounds are also embraced by the scope claimed.

As known, drugs suitable for the treatment of the different forms of depression are of very great importance in the treatment of patients with psychic disorders. Of the known compounds primarily the tricyclic antidepressants proved to be applicable for the treatment of the severe forms of depression. It is a great problem, however, that up to now there was known no antidepressant agent possessing prolonged effects, providing a stable blood level as a consequence of the retarded biotransformation and thus being applicable for the treatment of chronic diseases.

The above considerations hold also for neuroleptics with prolonged effects.

The invention aims at providing novel compounds with ergoline skeleton which can be used in the therapy as antidepressive or neuroleptic agents with prolonged activities.

The invention is based on the recognition that the $C_{6-12}$ carboxylic acid esters of the compounds having the formula

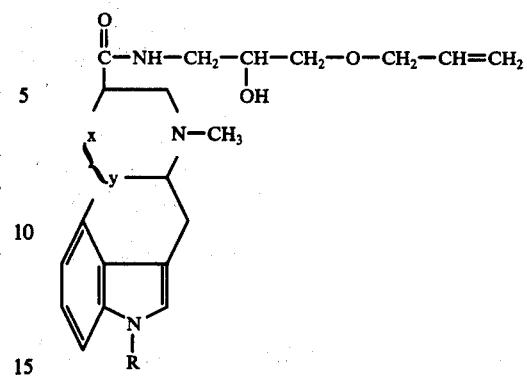
(II)

can be used to great advantage in the treatment of various psychic disorders as substances with prolonged effects.

Thus the invention relates to new compounds of the formula (I) as well as the pharmaceutically acceptable acid addition salts thereof, wherein R, $\widehat{x\ y}$ and n each have the same meanings as defined above. Of these compounds lysergic acid-(3'-allyloxy-2'-decanoyloxy-propyl)-amide

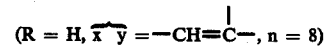

and its pharmaceutically acceptable acid addition salts are the most preferred ones.

As a process for the preparation of the new compounds having the formula (I), wherein R, $\widehat{x\ y}$ and n each have the same meanings as defined above, and the pharmaceutically acceptable acid addition salts thereof a compound of the formula (II), wherein R and $\widehat{x\ y}$ each have the same meanings as defined above, is acylated with a $C_{6-12}$ carboxylic acid or a $C_{6-12}$ carboxylic acid halide, and, if desired, the resulting ester is converted into its pharmaceutically acceptable acid addition salt with an organic or mineral acid.

According to a preferred method a $C_{6-12}$ acyl halide is used as acylating agent, and the acylation is performed in an organic solvent, in the presence of a base. As base e.g. a nitrogen-containing organic base, such as dicyclohexylamine, triethylamine, N-methylmorpholine or pyridine, whereas as organic solvent e.g. a ketone, tetrahydrofuran, dimethyl formamide, dioxane, pyridine or acetonitrile can be utilized. The acylation is performed at a temperature between −30° and +10° C, preferably at a temperature between −20° and 0° C. Of the acyl halides hexanecarbonyl chloride and capryl chloride are the most preferred acylating agents, whereas of the free carboxylic acids hexadecarboxylic acid and capric acid are the most preferred ones.

When using a free carboxylic acid as acylating agent, the acylation is performed preferably in an organic solvent, particularly in pyridine, in the presence of a water scavenger, preferably dicyclohexyl carbodiimide.

According to a preferred method lysergic acid-(3'-allyloxy-2'-oxy-propyl)-amide is dissolved in acetonitrile, and an acetone solution of capryl chloride and an acetone solution of dicyclohexylamine are added. The separated dicyclohexylammonium salt is filtered off, the filtrate is evaporated, the residue is admixed with water, and the aqueous mixture is extracted with a halogenated hydrocarbon. The extract is evaporated. If desired, the thus-obtained residue can be converted into its pharmaceutically acceptable non-toxic acid addition salt by treatment with an organic or mineral acid. The salt formation is effected preferably with maleic acid, hydrochloric acid, methanesulfonic acid or tartaric acid in an alcoholic medium.

The starting substances of the formula (II) can be prepared as follows: lysergic acid or a reactive derivative thereof, preferably the corresponding pentachlorophenyl ester is reacted with an amine having the formula

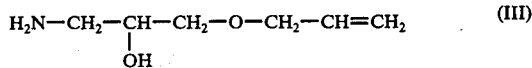

$$H_2N-CH_2-\underset{\underset{OH}{|}}{CH}-CH_2-O-CH_2-CH=CH_2 \quad (III)$$

according to the process described in Hungarian patent specification No. 163,546, and the obtained product is optionally subjected to N-methylation and/or hydrogenated in positions 9 and 10.

Lysergic acid-(3'-allyloxy-2'-decanoyloxy-propyl)-amide bimaleate, a new compound according to the invention, exerts a prolonged antidepressive effect when administered parenterally. This compound antagonizes the reserpine and tetrabenazine-provoked central nervous depressive phenomena in a manner analogous to the tricyclic antidepressants, but is far more potent than the latter compounds. The above compound also increases the effect of amphetamine. Lysergic acid-(3'-allyloxy-2'-decanoyloxy-propyl)-amide bimaleate differs in character from the tricyclic antidepressants to some extent, since it also exerts a slight psychostimulant effect on mice and rats. These effects appear in the oral or parenteral dosage range of from 1 to 10 mg./kg. The reserpine and tetrabenazine-antagonizing effects of the above compound appear shortly after the administration of the injection, and last for a prolonged period.

Lysergic acid-(3'-allyloxy-2'-decanoyloxy-propyl)-amide bimaleate can be used for the treatment of various psychic depressions in the form of an intramuscular depot injection containing 10 to 200 mg. of the active agent. This compound can be used to great advantage for the treatment of patients who require a prolonged treatment but tolerate the treatment poorly or are inconsistent in taking of the medicine. Depending on the dosage and the rate of biotransformation, a single dosage of the above compound may ensure a prolonged effect lasting for 1 to 4 weeks.

No side-effects occur upon the prolonged administration of the compounds according to the invention.

The new compounds according to the invention can be converted into pharmaceutical compositions by admixing them with inert, pharmaceutically acceptable carriers, diluents and/or auxiliary agents. As carrier or diluent primarily vegetable oils, such as olive oil, sesame oil and sunflower oil can be applied. The injectable compositions containing the new compounds of the formula (I) can be filled into ampoulles of 1 to 2 ml. volume, or vials of 5 to 10 ml. volume.

The thus-formed pharmaceutical compositions are used in the therapy as compositions ensuring prolonged effects. They can be administered preferably in a dosage of 12.5 to 100 mg. (0.5 to 2.0 ml) per 1 to 4 weeks.

The invention is elucidated in detail by the aid of the following non-limiting Examples.

EXAMPLE 1

Lysergic acid-(3'-allyloxy-2'-decanoyloxy-propyl)-amide bimaleate

Step A: Lysergic acid-(3'-allyloxy-2'-oxy-propyl)-amide 2.81 g. of lysergic acid hydrazide, dissolved in 100 ml. of 0.1 N hydrochloric acid, are added to 10 ml. of a 1 N aqueous sodium nitrite solution, and thereafter 15 ml. of 1 N hydrochloric acid are added dropwise to the stirred mixture at 2° to 5° C. The mixture is stirred for an additional 15 minutes at 0° to 5° C. Thereafter the mixture is neutralized with saturated sodium bicarbonate solution, and extracted in three portions with a total amount of 2l. of ether. The etheral fractions are combined, dried over anhydrous potassium carbonate, filtered, and a solution of 1.32 g. of 3-allyloxy-2-oxy-propylamine in 100 ml. of isopropanol are added to the stirred filtrate. The mixture is stirred at room temperature for 4 hours, and thereafter washed with water. The aqueous phase is extracted with 2x50 ml. of chloroform. The organic solutions are combined, dried over anhydrous potassium carbonate, and evaporated to dryness.

Step B: Lysergic acid-(3'-allyloxy-2'-decanoyloxy-propyl)-amide bimaleate 3.82 g. of lysergic acid-(3'-allyloxy-2'-oxy-propyl)-amide (free base) are dissolved in 150 ml. of acetonitrile with stirring, and a solution of 2.1 ml. of capryl chloride in 10 ml. of acetone is added dropwise to the stirred mixture at −10° C. The mixture is stirred and cooled for an additional hour. The separated salt is filtered off, and the filtrate is evaporated. 100 ml. of water and 200 ml. of chloroform are added to the residue, the pH of the aqueous phase is adjusted to 8 with 10% ammonium hydroxide solution, the mixture is shaken, and the organic phase is separated. The aqueous phase is extracted five times more with 100 ml. amounts of chloroform. The organic phases are combined, dried over anhydrous sodium sulfate, and evaporated to dryness. The dry residue is dissolved in ethanol and converted into its maleate. The thus-obtained lysergic acid-(3'-allylxoy-2'-decanoyloxy-propyl)-amide bimaleate melts at 160–162° C; $(\alpha)_D^{20} = +18.9°$ ($c = 0.5$, in 50% ethanol). Yield: 5.2 g. (80 %).

EXAMPLE 2

Lysergic acid-(3'-allyloxy-2'-enanthyloxy-propyl)-amide bimaleate 3.82 g. of lysergic acid-(3'-allyloxy-2'-oxy-propyl)-amide are dissolved in 150 ml. of pyridine with stirring. The solution is cooled to −20° C, and a solution of 10 ml. of enanthyl chloride in 15 ml. of acetone is added dropwise. The reaction mixture is stirred at −20° C for 30 minutes, then poured into 500 ml. of ice water, and 500 ml. of chloroform are added. The mixture is shaken, the organic phase is separated, and the aqueous phase is extracted with 6x50 ml. of chloroform. The organic phases are combined, dried over anhydrous sodium sulfate, filtered, and the filtrate is evaporated to dryness in vacuo. The residue is subjected to chromatography on a silica gel column (particle size of the filling agent: 0.09 to 0.16 mm.). A 90:4:30 mixture of chloroform, water and ethanol is used as eluting agent. The purified product is treated with an alcoholic solution of maleic acid. In this way 5.5 g. (85%) of lysergic acid-(3'-allyloxy-2'-enanthyloxy-propyl)-amide bimaleate are obtained: m.p.: 165°–167° C; $(\alpha)_D^{20} = +20°$ ($c = 0.5$, in 50% ethanol).

What we claim is:

1. A compound of the formula

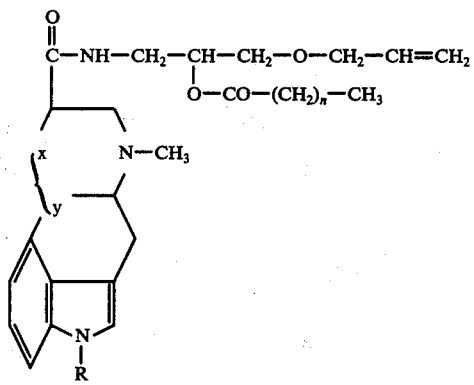

(I)

wherein R is hydrogen or methyl group, 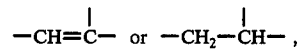 is a group of the formula $$-CH=\overset{|}{C}- \quad \text{or} \quad -CH_2-\overset{|}{CH}-,$$

and $n$ is an integer of from 4 to 10, or a pharmaceutically acceptable acid addition salt thereof.

2. A compound of the formula (I), wherein R and $x\,y$ each have the same meanings as defined in claim 1 and $n$ is equal to 8, or a pharmaceutically acceptable acid addition salt thereof.

3. Lysergic acid-(3'-allyloxy-2'-decanoyloxy-propyl)-amide or a pharmaceutically acceptable acid addition salt thereof.

4. A pharmaceutical composition having prolonged antidepressant effect, containing as active ingredient a compound as in claim 1, together with a pharmaceutically acceptable carrier, diluent and/or auxiliary agent.

5. A process for the preparation of a pharmaceutical composition, in which a compound as claimed in claim 1 is converted into a pharmaceutical composition by admixing it with a pharmaceutically acceptable carrier, diluent and/or auxiliary agent.

* * * * *